US007371519B2

(12) United States Patent
Wolber et al.

(10) Patent No.: US 7,371,519 B2
(45) Date of Patent: *May 13, 2008

(54) METHODS AND KITS FOR INDIRECT LABELING OF NUCLEIC ACIDS

(75) Inventors: Paul K. Wolber, Los Altos, CA (US); Karen W. Shannon, Los Gatos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 267 days.

This patent is subject to a terminal disclaimer.

(21) Appl. No.: 10/431,335

(22) Filed: May 6, 2003

(65) Prior Publication Data

US 2004/0005609 A1    Jan. 8, 2004

Related U.S. Application Data

(62) Division of application No. 09/861,035, filed on May 18, 2001, now Pat. No. 6,558,908, which is a division of application No. 09/495,152, filed on Jan. 31, 2000, now Pat. No. 6,235,483.

(51) Int. Cl.
*C12Q 1/68* (2006.01)
*C12P 19/34* (2006.01)

(52) U.S. Cl. .......................................... 435/6; 435/91.5

(58) Field of Classification Search ...................... None
See application file for complete search history.

(56) References Cited

U.S. PATENT DOCUMENTS

| | | | |
|---|---|---|---|
| 5,175,270 A | 12/1992 | Nilsen et al. | |
| 5,484,904 A | 1/1996 | Nilsen et al. | |
| 5,487,973 A | 1/1996 | Nilsen et al. | |
| 5,574,141 A | 11/1996 | Seliger et al. | |
| 5,604,097 A | 2/1997 | Brenner | |
| 5,635,400 A | 6/1997 | Brenner | |
| 5,695,934 A | 12/1997 | Brenner | |
| 5,716,785 A * | 2/1998 | Van Gelder et al. | 435/6 |
| 5,763,175 A | 6/1998 | Brenner | |
| 5,837,466 A | 11/1998 | Lane et al. | |
| 5,846,719 A | 12/1998 | Brenner | |
| 5,863,722 A | 1/1999 | Brenner | |
| 6,077,673 A | 6/2000 | Chenchik et al. | |
| 6,235,483 B1 * | 5/2001 | Wolber et al. | 435/6 |
| 6,238,865 B1 | 5/2001 | Huang et al. | |
| 6,261,770 B1 * | 7/2001 | Warthoe | 435/6 |
| 6,558,908 B2 * | 5/2003 | Wolber et al. | 435/6 |
| 2001/0026919 A1 * | 10/2001 | Chenchik et al. | 435/6 |
| 2004/0209376 A1 * | 10/2004 | Natan et al. | 436/56 |
| 2005/0158772 A1 * | 7/2005 | Lockhart et al. | 435/6 |

FOREIGN PATENT DOCUMENTS

| | | |
|---|---|---|
| WO | WO 9727317 A1 * | 7/1997 |
| WO | WO 97/31256 | 8/1997 |
| WO | WO 98/24933 | 6/1998 |

OTHER PUBLICATIONS

Lombardo et al. Altered brain sodium channel transcript levels in human epilepsy. Molecular Brain Research, vol. 35, Issues 1-2, Jan. 1996, pp. 84-90.*
"Population." Merriam-Webster Online Dictionary. 2004. http://www.merriam-webster.com (Jan. 2, 2004). Two printed pages. Accessed Aug. 14, 2006.*
Lost Springs, Wyoming. (Jul. 8, 2006). In Wikipedia, The Free Encyclopedia. Retrieved 15:09, Aug. 14, 2006, from http://en.wikipedia.org/w/index.php?title=Lost_Springs%2C_Wyoming&oldid=62708768. One printed page.*
"Group." Merriam-Webster Online Dictionary. 2004. http://www.merriam-webster.com (Jan. 2, 2004.) Two printed pages. Accessed Aug. 14, 2006.*
Zhou et al. New primer strategy improves precision of differential display. BioTechniques (1995) 18(5): 842-844, 846, 848, 850.*
"Genisphere—A Datascope Company: 3DNA Submicro Expression Array Detection Kit," http://www.genisphere.com/pdf/submicro.pdf, boaring a notice "2000, Genisphere, Inc. All rights reserved".
"3DNA Products: 3DNA Submicro Expression Array Detection Kits," http://www.genisphere.com/ExpressionArrays.html, bearing a 1998-99 copyright notice.
Ahern. Biochemical, Reagents Kits Offer Scientist Good Return on Investment The Scientist, vol. 9, No. 15. pp. 1-9.
Velculescu et al. Serial Analysis of Gene Expression. Science, vol. 270, pp. 484-487, 1995.

* cited by examiner

*Primary Examiner*—Kenneth R. Horlick
*Assistant Examiner*—Angela Bertagna

(57) ABSTRACT

Methods and kits for labeling nucleic acids are provided. In the subject methods, an oligonucleotide tagged nucleic acid comprising an oligonucleotide tag is first generated. The oligonucleotide tagged nucleic acid is then contacted under hybridization conditions with a labeled oligonucleotide complementary to the oligonucleotide tag, yielding a labeled nucleic acid. The kits of the subject invention at least include a primer for use in enzymatically generating an oligonucleotide tagged target nucleic acid, where the primer generally at least includes an oligo dT region and the oligonucleotide tag, and a labeled oligonucleotide complementary to the oligonucleotide tag. The subject methods and kits find use in a variety of applications, and are particularly suited for use in gene expression analysis applications.

24 Claims, No Drawings

SEQUENCE LISTING

```
<160> NUMBER OF SEQ ID NOS: 6

<210> SEQ ID NO 1
<211> LENGTH: 71
<212> TYPE: DNA
<213> ORGANISM: Artificial Sequence
<220> FEATURE:
<223> OTHER INFORMATION: synthetic oligonucleotide

<400> SEQUENCE: 1
aattaatacg actcactata gggagattta cgctactcat cgccggcgcc tacgttttt      60 tttttttttt t                                                          71

<210> SEQ ID NO 2
<211> LENGTH: 71
<212> TYPE: DNA
<213> ORGANISM: Artificial Sequence
<220> FEATURE:
<223> OTHER INFORMATION: synthetic oligonucleotide

<400> SEQUENCE: 2
aattaatacg actcactata gggagattca ttacctacgt cggcgccgcg ctactttttt      60
tttttttttt t                                                          71

<210> SEQ ID NO 3
<211> LENGTH: 27
```

-continued

```
<212> TYPE: DNA
<213> ORGANISM: Artificial Sequence
<220> FEATURE:
<223> OTHER INFORMATION: synthetic oligonucleotide

<400> SEQUENCE: 3
cgtaggcgcc ggcgatgagt agcgtaa                                               27

<210> SEQ ID NO 4
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 4
cgtaggcgcc ggcgatgagt agcgtaa                                               27

<210> SEQ ID NO 5
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 5
gtagcgcggc gccgacgtag gtaatga                                               27

<210> SEQ ID NO 6
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 6
gtagcgcggc gccgacgtag gtaatga                                               27
```

METHODS AND KITS FOR INDIRECT LABELING OF NUCLEIC ACIDS

This is a divisional of application Ser. No. 09/861,035 filed on May 18, 2001 now U.S. Pat. No. 6,558,908, which is a divisional of application Ser. No. 09/495,152, filed on Jan. 31, 2000, now U.S. Pat. No. 6,235,483, the entire disclosure of which is incorporated into this application by reference.

TECHNICAL FIELD

The technical field of this invention is nucleic acid labeling, particularly in the field of gene expression analysis.

BACKGROUND OF THE INVENTION

The characterization of cellular gene expression finds application in a variety of disciplines, such as in the analysis of differential expression between different tissue types, different stages of cellular growth or between normal and diseased states. Fundamental to differential expression analysis is the detection of different mRNA species in a test population, and at least the qualitative, if not quantitative, determination of different mRNA levels in that test population.

In many currently employed gene expression analysis protocols, detection of different mRNA levels involves the steps of generating an image or target nucleic acid population that is representative of the mRNA population of the test sample. In other words, a population of image nucleic acids is generated where the population is indicative of the different mRNAs that are originally present in the sample. The image may be DNA or RNA and may have the sequence of initial mRNA or the complement thereof. Following generation, the population of image or target nucleic acids is hybridized to an array of probe nucleic acids stably associated with the surface of a solid support. Since the sequence and location of each probe is known, any resultant hybridization complexes that form on the array surface between target and probe can be used to identify those genes that are expressed in the cell from which the initial mRNA sample was obtained. Since the methods require detection of target/probe complexes on the array surface, the target nucleic acids are generally labeled so that they can be detected. Of increasing interest is the use of fluorescent labels for target nucleic acid labeling.

There are generally two ways of labeling image or target nucleic acids with fluorescent labels—direct fluorescent labeling protocols and indirect fluorescent labeling protocols. In the case of direct fluorescent labeling, a fluorescently labeled chemical analog of one or more of the four nucleoside triphosphates (henceforth called nucleotides) is present during the enzymatic generation of the image or target nucleic acid, which results in incorporation of the labeled nucleotide into the polymerized nucleic acid and consequent direct fluorescent labeling of the nucleic acid. While direct fluorescent labeling is employed in many protocols, there are disadvantages associated with this approach. First, not all available fluorophores are amenable to incorporation into the image polynucleotide during its generation, i.e. not all fluorophore-labeled nucleotides are efficiently incorporated by nucleic acid polymerases, which limits the availability of useable labels. Second, fluorescently labeled nucleotides that are capable of being processed by nucleic acid polymerases are not processed efficiently, resulting in significant waste of reagents and costs associated therewith. In addition, the fluorescently labeled nucleotides are often expensive.

In order to address at least some of the above disadvantages associated with direct fluorescence labeling techniques, indirect fluorescent labeling protocols have been developed. In one type of indirect fluorescent labeling protocol, nucleotides modified with chemical tags, e.g. biotin, are employed in the image nucleic acid generation step. Next, either during or after hybridization, a fluorescent label modified to specifically bind to the chemical tag, e.g. streptavidin conjugated fluorescent label, is contacted with the image or target nucleic acid, thereby providing indirect fluorescent labeling. While indirect labeling protocols such as those described above overcome some of the disadvantages of direct labeling protocols, they are not entirely satisfactory. For example, such protocols are not readily adaptable to "two color" gene expression analyses, in which two different populations of target nucleic acids are hybridized to the same array and distinguished from each other by means of distinguishable labels.

Accordingly, there is interest in the development of improved methods of indirectly fluorescently labeling image or target nucleic acids for use in gene expression analyses. Of particular interest would be the development of an indirect labeling protocol suited for use with two color hybridization procedures in which mixed populations of two or more different image polynucleotides which do not include chemically modified nucleotide residues can be labeled with distinguishable fluorescent labels.

Relevant Literature

U.S. Patents of interest include: U.S. Pat. Nos. 5,604,097; 5,635,400; 5,695,934; 5,763,175; 5,863,722; and 5,846,719. Also of interest are: WO 97/31256 and WO 98/24933.

SUMMARY OF THE INVENTION

Methods and kits for labeling nucleic acids are provided. In the subject methods, the first step is to generate an oligonucleotide tagged nucleic acid, where the tagged target includes an oligonucleotide tag. The oligonucleotide tagged nucleic acid is then contacted under hybridization conditions with a labeled oligonucleotide complementary to the oligonucleotide tag, yielding a labeled nucleic acid. Where the method is part of a gene expression analysis assay, a three part hybridization complex made up of the tagged target, the labeled oligonucleotide and a probe oligonucleotide is produced and detected. The detected three part hybridization complex is then related to the expression of a particular gene in the cell from which the target was derived. The kits of the subject invention at least include a primer for use in enzymatically generating an oligonucleotide tagged target nucleic acid, where the primer generally at least includes an oligo dT region and the oligonucleotide tag, and a labeled oligonucleotide complementary for the oligonucleotide tag. The subject methods and kits find use in a variety of applications, and are particularly suited for use in labeling image or target nucleic acids in gene expression analysis applications.

DEFINITIONS

The term "nucleic acid" as used herein means a polymer composed of nucleotides, e.g. deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

DESCRIPTION OF THE SPECIFIC EMBODIMENTS

Methods and kits for labeling nucleic acids are provided. In the subject methods, an oligonucleotide tagged nucleic acid comprising an oligonucleotide tag is first generated. The oligonucleotide tagged nucleic acid is then contacted under hybridization conditions with a labeled oligonucleotide complementary to the oligonucleotide tag, yielding an indirectly labeled nucleic acid. The kits of the subject invention at least include a primer for use in enzymatically generating an oligonucleotide tagged target nucleic acid, where the primer generally at least includes an oligo dT region and the oligonucleotide tag, and a labeled oligonucleotide complementary for the oligonucleotide tag. The subject methods and kits find use in a variety of applications, and are particularly suited for use in labeling image or target nucleic acids in gene expression analysis applications, including two color expression analyses. In further disclosing the subject invention, the methods will be discussed first in greater detail, followed by a more detailed description of the subject kits that find use in practicing the methods of the present invention.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a", "an" and "the" include plural reference unless the context clearly dictates otherwise. Unless defined otherwise all technical and scientific terms used herein have the same meaning as commonly understood to one of ordinary skill in the art to which this invention belongs.

Methods

As summarized above, the subject invention provides a method for indirectly labeling a nucleic acid, e.g. with a fluorescent label. While the subject methods may be used to indirectly label any type of nucleic acid, they are particularly suited for use in labeling image or target nucleic acids in gene expression analysis applications. As such, the invention is now further described in terms of labeling image or target nucleic acids in gene expression analysis applications. However, it is to be understood that the below description is illustrative of a particular application of the subject method for indirect labeling of a nucleic acid which is suitable for labeling any type of nucleic acid in any type of application.

Where the subject methods are used in gene expression analyses, the first step is to generate a population of oligonucleotide tagged target nucleic acids from an initial mRNA source or sample. By oligonucleotide tagged target nucleic acid is meant a nucleic acid that has: (a) a sequence which is either the same as, or complementary to, the sequence of an mRNA found in an initial sample, where the target may be DNA or RNA and be present in amplified amounts as compared to the initial amount of mRNA; and (b) an oligonucleotide tag. The oligonucleotide tag comprises a nucleotide base sequence that is capable of hybridizing to an oligonucleotide label, described in greater detail below, to produce a duplex with a high melting temperature. The length of the oligonucleotide tag is at least about 15 bases, usually at least about 20 bases and more usually at least about 25 bases, and may be as long as 80 bases or longer, but usually does not exceed about 65 bases and more usually does not exceed about 60 bases.

While in the broadest sense the oligonucleotide tag may have any random sequence, the following parameters are preferably employed to identify an appropriate oligonucleotide tag. First, the oligonucleotide sequence should be a sequence which is rare with respect to sequences present in organism from which the mRNA sample and target nucleic acid is derived. For example, where the oligonucleotide tag is employed to tag image or target nucleic acids derived from an initial yeast mRNA sample, the oligonucleotide tag should have a sequence that is rare in yeast. Rarity of a particular sequence, and therefore its suitability for use as an oligonucleotide tag, can be identified using any convenient sequence similarity comparison tool, such as BLAST searches, and the like. In addition, the sequence should possess minimal self structure, e.g. it should not form hairpin loops or other secondary structures. Finally, as indicated above, the sequence should be one that exhibits a high melting temperature when hybridized to its complementary sequence, e.g. a complementary labeled oligonucleotide. By high melting temperature is meant a temperature that at least exceeds 60° C., where the temperature preferable exceeds about 65° C. and more preferably exceeds about 70° C. Oligonucleotide tags suitable for use in the present invention can be designed manually or with the assistance of a computing means, in which an algorithm is employed that is capable of identifying sequences that satisfy the above described parameters. Typically, the algorithm is recorded on a computer readable storage medium, where such media are well known to those of skill in the art.

In the subject methods, the oligonucleotide tagged target or image nucleic acids are produced generally through enzymatic generation protocols. Specifically, the oligonucleotide tagged target nucleic acids are typically produced using template dependent polymerization protocols and an initial mRNA source. The initial mRNA may be present in a variety of different samples, where the sample will typically be derived from a physiological source. The physiological source may be derived from a variety of eukaryotic sources, with physiological sources of interest including sources derived from single-celled organisms such as yeast and multicellular organisms, including plants and animals, particularly mammals, where the physiological sources from multicellular organisms may be derived from particular organs or tissues of the multicellular organism, or from isolated cells derived therefrom. In obtaining the sample of RNA to be analyzed from the physiological source from which it is derived, the physiological source may be subjected to a number of different processing steps, where such processing steps might include tissue homogenization, cell isolation and cytoplasm extraction, nucleic acid extraction and the like, where such processing steps are known to those of skill in the art. Methods of isolating RNA from cells, tissues, organs or whole organisms are known to those of skill in the art and are described in Maniatis et al. (1989), Molecular Cloning: A Laboratory Manual 2d Ed. (Cold Spring Harbor Press). Alternatively, at least some of the initial steps of the subject methods may be performed in situ, as described in U.S. Pat. No. 5,514,545, the disclosure of which is herein incorporated by reference.

A number of different enzymatic protocols exist for generating image or target nucleic acids from an initial mRNA sample are known and continue to be developed. Any convenient protocol may be employed, where the particular protocol employed depends, at least in part, on a number of factors, including: whether one wants to generate amplified amounts of target or image nucleic acid; whether one wants to generate geometrically or linearly amplified amounts of target nucleic acid; whether bias in the amount of target can be tolerated, etc. A common feature of the protocols that find use in preparing the oligonucleotide tagged image or target nucleic acids of the subject invention is the use of at least one oligonucleotide primer. The sequence of the primer employed may vary depending on which method is employed for enzymatic generation of the oligonucleotide tagged target. However, the primers typically include the oligonucleotide tag and a region complementary to a region of the mRNA template, e.g. an oligo dT region.

A number of nucleic acid amplification methods can be employed to generate the oligonucleotide tagged target nucleic acid from an initial mRNA source. Such methods include the "polymerase chain reaction" (PCR) as described in U.S. Pat. No. 4,683,195, the disclosure of which is herein incorporated by reference, and a number of transcription-based exponential amplification methods, such as those described in U.S. Pat. Nos. 5,130,238; 5,399,491; and 5,437,990; the disclosures of which are herein incorporated by reference. Each of these methods uses primer-dependent nucleic acid synthesis to generate a DNA or RNA product, which serves as a template for subsequent rounds of primer-dependent nucleic acid synthesis. Each process uses (at least) two primer sequences complementary to different strands of a desired nucleic acid sequence and results in an exponential increase in the number of copies of the target sequence. Where the above exponential amplification procedures are employed, at least one of the two primers employed in each round of amplification will comprise sequence corresponding to the oligonucleotide tag, e.g. sequence that is the same as the sequence of the oligonucleotide tag employed in first strand cDNA synthesis or sequence that is complementary thereto.

Alternatively, amplification methods that utilize a single primer may be employed to generate oligonucleotide tagged target or image nucleic acids from an initial mRNA sample. See e.g. U.S. Pat. Nos. 5,554,516; and 5,716,785; the disclosures of which are herein incorporated by reference. The methods reported in these patents utilize a single primer containing an RNA polymerase promoter sequence and a sequence complementary to the 3'-end of the desired nucleic acid target sequence(s) ("promoter-primer"). In both methods, the promoter-primer is added under conditions where it hybridizes to the target sequence(s) and is converted to a substrate for RNA polymerase. In both methods, the substrate intermediate is recognized by RNA polymerase, which produces multiple copies of RNA complementary to the target sequence(s) ("cRNA"). Each method uses, or could be adapted to use, a primer containing poly-dT for amplification of heterogeneous mRNA populations. In these linear amplification methods, the promoter primer is generally further characterized by the presence of the oligonucleotide tag, which tag element or domain is positioned between the promoter and the mRNA complementary region, e.g. oligo dT region.

Of particular interest in many embodiments is the use of the following linear amplification protocol to generate oligonucleotide tagged target nucleic acid for use in the subject methods. The following method is a method for linearly amplifying mRNA into its RNA complement (cRNA), which cRNA may then be used as target or image nucleic acid. In other words, it is a method of producing amplified amounts of cRNA from an initial amount of mRNA. By amplified amounts is meant that for each initial mRNA in a given sample, multiple corresponding cRNAs, where the term cRNA is defined here as ribonucleic acid complementary to the initial mRNA, are produced. By corresponding is meant that the cRNA shares a substantial amount of sequence identity with the sequence complementary to the mRNA (i.e. the complement of the initial mRNA), where substantial amount means at least 95% usually at least 98% and more usually at least 99%, where sequence identity is determined using the BLAST algorithm, as described in Altschul et al. (1990), J. Mol. Biol. 215:403-410 (using the published default setting, i.e. parameters w=4, t=17). Generally, the number of corresponding cRNA molecules produced for each initial mRNA during the subject linear amplification methods will be at least about 10, usually at least about 50 and more usually at least about 100, where the number may be as great as 600 or greater, but often does not exceed about 1000.

In the first step of this linear amplification method, an initial mRNA sample is subjected to a series of enzymatic reactions under conditions sufficient to ultimately produce double-stranded DNA for each initial mRNA in the sample that is amplified. During this first step, an RNA polymerase promoter region and the oligonucleotide tag is incorporated into the resultant product. Depending on the nature of the primer employed during first strand synthesis, as described in greater detail below, the subject methods can be used to produce amplified amounts of cRNA corresponding to substantially all of the mRNA present in the initial sample, or to a proportion or fraction of the total number of distinct mRNAs present in the initial sample. By substantially all of the mRNA present in the sample is meant more than 90%, usually more than 95%, where that portion not amplified is solely the result of inefficiencies of the reaction and not intentionally excluded from amplification.

The promoter-primer employed in the amplification reaction includes: (a) a poly-dT region for hybridization to the poly-A tail of the mRNA; (b) an RNA polymerase promoter region 5' of the -poly-dT region that is in an orientation capable of directing transcription of cRNA; and (c) an oligonucleotide tag, as described above, positioned between the promoter region and the poly-dT region. As such, the primer-promoter employed to generate the target in this particular preferred method is more accurately referred to as a primer-tag-promoter. In certain embodiments, the primer will be a "lock-dock" primer, in which immediately 3' of the poly-dT region is either a "G', "C", or "A" such that the primer has the configuration of 3'-VTTTTTTTT . . . 5', where V is "G", "C", or "A". The poly-dT region is sufficiently long to provide for efficient hybridization to the poly-A tail, where the region typically ranges in length from 10-50 nucleotides in length, usually 10-25 nucleotides in length, and more usually from 14 to 20 nucleotides in length.

A number of RNA polymerase promoters may be used for the promoter region of the first strand cDNA primer, i.e. the promoter-tag-primer. Suitable promoter regions will be capable of initiating transcription from an operationally linked DNA sequence in the presence of ribonucleotides and an RNA polymerase under suitable conditions. The promoter region will usually comprise between about 15 and 250 nucleotides, preferably between about 17 and 60 nucleotides, from a naturally occurring RNA polymerase promoter or a consensus promoter region, as described in Alberts et al. (1989) in Molecular Biology of the Cell, 2d Ed. (Garland Publishing, Inc.). In general, prokaryotic promoters are preferred over eukaryotic promoters, and phage or virus promoters most preferred. As used herein, the term "operably linked" refers to a functional linkage between the affecting sequence (typically a promoter) and the controlled sequence (the mRNA binding site). The promoter regions that find use are regions that result in highly specific binding of the RNA polymerase to the template DNA and that contain the start site and signal for RNA synthesis to begin. A wide variety of promoters are known and many are very well characterized. Representation promoter regions of particular interest include T7, T3 and SP6 late promoters, as described in Chamberlin and Ryan, The Enzymes (ed. P. Boyer, Academic Press, New York) (1982) pp 87-108.

Where one wishes to amplify only a portion of the mRNA species in the sample, one may optionally provide for a short arbitrary sequence 3' of the poly- dT region, where the short arbitrary sequence will generally be less than 5 nucleotides in length and usually less than 2 nucleotides in length, where the dNTP immediately adjacent to the poly-dT region will not be a T residue and usually the sequence will comprise no T residue. Such short 3' arbitrary sequences are described in Ling and Pardee (1992), Science 257, 967.

Any of the primers employed in the above methods, including the promoter-tag-primer described above, may be prepared using any suitable method, such as, for example, the known phosphotriester and phosphite triester methods, or automated embodiments thereof. In one such automated embodiment, dialkyl phosphoramidites are used as starting materials and may be synthesized as described by Beaucage et al. (1981), Tetrahedron Letters 22, 1859. One method for synthesizing oligonucleotides on a modified solid support is described in U.S. Pat. No. 4,458,066; the disclosure of which is herein incorporated by reference. It is also possible to use a primer that has been isolated from a biological source (such as a restriction endonuclease digest). The primers herein are selected to be "substantially" complementary to each specific sequence to be amplified, i.e.; the primers should be sufficiently complementary to hybridize to their respective targets. Therefore, the primer sequence need not reflect the exact sequence of the target, and can, in fact be "degenerate." Non-complementary bases or longer sequences can be interspersed into the primer, provided that the primer sequence has sufficient complementarity with the sequence of the target to be amplified to permit hybridization and extension.

In the first step of this preferred linear amplification method for the generation of oligonucleotide tagged image or target nucleic acids from an initial mRNA source, the oligonucleotide promoter-tag-primer is hybridized with an initial mRNA sample and the primer-mRNA hybrid is converted to a double-stranded cDNA product that is recognized by an RNA polymerase. The promoter-tag-primer is contacted with the mRNA under conditions that allow the poly-dT site to hybridize to the poly-A tail present on most eukaryotic mRNA species. The catalytic activities required to convert the primer-mRNA hybrid to double-stranded cDNA are an RNA-dependent DNA polymerase activity, a RNaseH activity, and a DNA-dependent DNA polymerase activity. Most reverse transcriptases, including those derived from Moloney murine leukemia virus (MMLV-RT), avian myeloblastosis virus (AMV-RT), bovine leukemia virus (BLV-RT), Rous sarcoma virus (RSV) and human immunodeficiency virus (HIV-RT) catalyze each of these activities. These reverse transcriptases are sufficient to convert primer-mRNA hybrid to double-stranded DNA in the presence of additional reagents which include, but are not limited to: dNTPs; monovalent and divalent cations, e.g. KCl, $MgCl_2$; sulfhydryl reagents, e.g. dithiothreitol; and buffering agents, e.g. Tris-Cl. Alternatively, a variety of proteins that catalyze one or two of these activities can be added to the cDNA synthesis reaction. For example, MMLV reverse transcriptase lacking RNaseH activity (described in U.S. Pat. No. 5,405,776) which catalyzes RNA-dependent DNA polymerase activity and DNA-dependent DNA polymerase activity, can be added with a source of RNaseH activity, such as the RNaseH purified from cellular sources, including *Escherichia coli*. These proteins may be added together during a single reaction step, or added sequentially during two or more substeps. Finally, additional proteins that may enhance the yield of double-stranded DNA products may also be added to the cDNA synthesis reaction. These proteins include a variety of DNA polymerases (such as those derived from *E. coli*, thermophilic bacteria, archaebacteria, phage, yeasts, Neurosporas, Drosophilas, primates and rodents), and DNA Ligases (such as those derived from phage or cellular sources, including T4 DNA Ligase and *E. coli* DNA Ligase).

Conversion of primer-mRNA hybrid to double-stranded cDNA by reverse transcriptase proceeds through an RNA:DNA intermediate which is formed by extension of the hybridized promoter-primer by the RNA-dependent DNA polymerase activity of reverse transcriptase. The RNaseH activity of the reverse transcriptase then hydrolyzes at least a portion of the RNA:DNA hybrid, leaving behind RNA fragments that can serve as primers for second strand synthesis (Meyers et al., Proc. Nat'l Acad. Sci. USA (1980) 77:1316 and Olsen & Watson, Biochem. Biophys. Res. Commun. (1980) 97:1376). Extension of these primers by the DNA-dependent DNA polymerase activity of reverse transcriptase results in the synthesis of double-stranded cDNA. Other mechanisms for priming of second strand synthesis may also occur, including "self-priming" by a hairpin loop formed at the 3' terminus of the first strand cDNA (Efstratiadis et al. (1976), Cell 7, 279; Higuchi et al. (1976), Proc. Natl, Acad, Sci USA 73, 3146; Maniatis et al. (1976), Cell 8, 163; and Rougeon and Mach (1976), Proc. Natl. Acad. Sci. USA 73, 3418; and "non-specific priming" by other DNA molecules in the reaction, i.e. the promoter-primer.

The second strand cDNA synthesis results in the creation of a double-stranded promoter region. The second strand cDNA includes not only a sequence of nucleotide residues that comprise a DNA copy of the mRNA template, but also additional sequences at its 3' end which are complementary to the promoter-tag-primer used to prime first strand cDNA synthesis. The double-stranded promoter region serves as a recognition site and transcription initiation site for RNA polymerase, which uses the second strand cDNA as a template for multiple rounds of RNA synthesis during the next stage of the subject methods.

Depending on the particular protocol, the same or different DNA polymerases may be employed during the cDNA synthesis step. In a preferred embodiment, a single reverse transcriptase, most preferably MMLV-RT, is used as a source of all the requisite activities necessary to convert primer-mRNA hybrid to double-stranded cDNA. In another preferred embodiment, the polymerase employed in first strand cDNA synthesis is different from that which is employed in second strand cDNA synthesis. Specifically, a reverse transcriptase lacking RNaseH activity (e.g. Superscript II™) is combined with the primer-mRNA hybrid during a first substep for first strand synthesis. A source of RNaseH activity, such as *E. coli* RNaseH or MMLV-RT, but most preferably MMLV-RT, is added during a second substep to initiate second strand synthesis. In yet other embodiments, the requisite activities are provided by a plurality of distinct enzymes. The manner is which double-stranded cDNA is produced from the initial mRNA is not critical to certain embodiments of the invention. However, the preferred embodiments use MMLV-RT, or a combination of Superscript II™ and MMLV-RT, or a combination of Superscript II™ and *E. coli* RNaseH, for cDNA synthesis as these embodiments yield certain desired results. Specifically, in the preferred embodiments, reaction conditions are chosen so that enzymes present during the cDNA synthesis do not adversely affect the subsequent transcription reaction. Potential inhibitors include, but are not limited to, RNase contaminants of certain enzyme preparations.

The next step of this preferred linear amplification method is the preparation of cRNA from the double-stranded cDNA prepared in the first step. During this step, the double-stranded cDNA produced in the first step is transcribed by RNA polymerase to yield cRNA, which is complementary to the initial mRNA target from which it is amplified and includes the oligonucleotide tag. A critical feature of the invention is that this second step is carried out in the presence of reverse transcriptase which is present in the reaction mixture from the first step. Thus, the subject methods do not involve a step in which the double-stranded cDNA is physically separated from the reverse transcriptase following double-stranded cDNA preparation. Critical to the subject methods is that the reverse transcriptase that is present during the transcription step is rendered inactive. Thus, the transcription step is carried out in the presence of a reverse transcriptase that is unable to catalyze RNA-dependent DNA polymerase activity, at least for the duration of the transcription step. As a result, the cRNA products of the transcription reaction cannot serve as substrates for additional rounds of amplification, and the amplification process cannot proceed exponentially.

The reverse transcriptase present during the transcription step may be rendered inactive using any convenient protocol. The transcriptase may be irreversibly or reversibly rendered inactive. Where the transcriptase is reversibly rendered inactive, the transcriptase is physically or chemically altered so as to no longer able to catalyze RNA-dependent DNA polymerase activity. The transcriptase may be irreversibly inactivated by any convenient means. Thus, the reverse transcriptase may be heat inactivated, in which the reaction mixture is subjected to heating to a temperature sufficient to inactivate the reverse transcriptase prior to commencement of the transcription step. In these embodiments, the temperature of the reaction mixture and therefore the reverse transcriptase present therein is typically raised to 55° C. to 70° C. for 5 to 60 minutes, usually to about 65° C. for 15 to 20 minutes. Alternatively, reverse transcriptase may irreversibly inactivated by introducing a reagent into the reaction mixture that chemically alters the protein so that it no longer has RNA-dependent DNA polymerase activity. In yet other embodiments, the reverse transcriptase is reversibly inactivated. In these embodiments, the transcription may be carried out in the presence of an inhibitor of RNA-dependent DNA polymerase activity. Any convenient reverse transcriptase inhibitor may be employed which is capable of inhibiting RNA-dependent DNA polymerase activity a sufficient amount to provide for linear amplification. However, these inhibitors should not adversely affect RNA polymerase activity. Reverse transcriptase inhibitors of interest include ddNTPs, such as ddATP, ddCTP, ddGTP or ddTTP, or a combination thereof, the total concentration of the inhibitor typically ranges from about 50 μM to 200 μM.

For this transcription step, the presence of the RNA polymerase promoter region on the double-stranded cDNA is exploited for the production of cRNA. To synthesize the cRNA, the double-stranded DNA is contacted with the appropriate RNA polymerase in the presence of the four ribonucleotides, under conditions sufficient for RNA transcription to occur, where the particular polymerase employed will be chosen based on the promoter region present in the double-stranded DNA, e.g. T7 RNA polymerase, T3 or SP6 RNA polymerases, *E. coli* RNA polymerase, and the like. Suitable conditions for RNA transcription using RNA polymerases are known in the art, see e.g. Milligan and Uhlenbeck (1989), Methods in Enzymol. 180, 51. As mentioned above, a critical feature of the subject methods is that this transcription step is carried out in the presence of a reverse transcriptase that has been rendered inactive, e.g. by heat inactivation or by the presence of an inhibitor.

The resultant cRNA produced by the above preferred linear amplification method is characterized by including, in addition to sequences corresponding to the original mRNA sample, an oligonucleotide tag. The cRNA produced as described above may then be used as the oligonucleotide tagged image or target nucleic acid in the subject methods.

Whatever process is employed to generate the tagged target nucleic acid, where representative protocols have been provided immediately above, a critical feature is that chemical analogs of nucleotides that have been modified to include a label moiety, e.g. an organic fluorophore, an isotopic label, a capture ligand, e.g. biotin, etc., are not employed. As a result, the tagged target nucleic acid produced in this first step does not include any nucleotide residues that have been modified to include a label moiety, as described above. A further critical feature of the subject target generation methods is that a ligation step is not employed. In other words, a step where two oligonucleotides are ligated to each other using a ligase activity is not employed.

Following generation of the oligonucleotide tagged target or image nucleic acids, as described above, the next step in the subject methods of gene expression analysis is to produce a three part hybridization complex that is made up of: (a) the oligonucleotide tagged target nucleic acid; (b) the probe nucleic acid; and (c) a labeled oligonucleotide complementary to the oligonucleotide tag. By three part hybridization complex is meant that the three components of the complex are stably associated with each other through hydrogen bonds formed between complementary bases of the various components, i.e. through Watson & Crick hybridization of the various components to each other. A critical feature of the subject three part complexes is that the labeled is present on a part distinct from the target nucleic acid, i.e. the label is covalently bound to a strand that is not the same as the target nucleic acid. As such, a complex in which the label is present on the same strand as the target is not produced by the subject methods. Accordingly, the target nucleic acid is indirectly labeled in the three part complex.

The probe nucleic acid of the above described three part hybridization complexes may be any nucleic acid that is complementary to, and hybridizes to, a portion or region of the oligonucleotide tagged image or target nucleic acid, so long as it does not hybridize to the oligonucleotide tag domain of the oligonucleotide tagged target nucleic acid. The length of the probe nucleic acid may vary greatly, but is generally at least about 15 bases long, usually at least about 20 bases long and more usually at least about 25 bases long, where in certain embodiments the probe may be as long as 50 bases or longer, but generally does not exceed about 75 bases in length and usually does not exceed about 60 bases in length. In many embodiments, the probe nucleic acid is stably associated with the surface of a solid support, e.g. a bead, planar substrate, etc. In many preferred embodiments, the probe nucleic acid is present on an array of probe nucleic acids stably associated with the surface of a solid support. A variety of probe nucleic acid arrays have been developed and are known to those of skill in the art, where such arrays include those described in: U.S. Pat. Nos. 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,695; 5,624,711; 5,639,603; 5,658,734; WO 93/17126; WO 95/11995; WO 95/35505; EP 742 287; and EP 799 897; the disclosures of which are herein incorporated by reference. A critical feature of each array is that the identity of each probe, e.g. the gene to which the probe corresponds, is known at each location of the array.

The labeled oligonucleotide component of the above described three part hybridization complexes is a labeled oligonucleotide that hybridizes to the oligonucleotide tag domain to produce a duplex that has a high melting temperature. The length of the labeled oligonucleotide will be substantially the same as that of the oligonucleotide tag, where any difference in length generally does not exceed about 5 bases, and usually does not exceed about 3 bases. As such, the length of the labeled nucleotide generally ranges from about 15 bases to 80 bases, usually from about 20 bases to 65 bases and more usually from about 25 bases to 60 bases. The sequence of the oligonucleotide is substantially, if not completely, complementary to the sequence of its corresponding oligonucleotide tag. As such, the number of mismatched bases, if any, between the labeled oligonucleotide and its corresponding oligonucleotide tag does not exceed about 2, and usually does not exceed about 1. As mentioned above, the sequence of the labeled oligonucleotide is selected such that any hybridized duplex produced between it and its corresponding oligonucleotide tag has a high melting temperature, where by high melting temperature is meant a temperature in excess of at least about 60° C., usually at least about 65° C. and more usually at least about 70° C.

A critical feature of the labeled oligonucleotide is the label. In the labeled oligonucleotide, one or more nucleotide residues is modified to include a label. In principle, the label may be directly or indirectly detectable. However, in many preferred embodiments, the label is a directly detectable label, by which is meant that it need not react with another chemical reagent or molecule in order to provide a detectable signal. One type of directly detectable label is an isotopic label, in which one or more of the nucleotides is labeled with a radioactive label, such as $^{32}S$, $^{32}P$, $^{3}H$, or the like. In yet other embodiments, light scattering particles may be employed as the label. In many preferred embodiments, the directly detectable label is a fluorescent label. Fluorescent labels of interest (in various chemically conjugable forms) include: fluorescein, rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), the cyanine dyes, such as Cy3, Cy5, Alexa 542, Bodipy 630/650, fluorescent particles, fluorescent semiconductor nanocrystals, and the like. The labeled oligonucleotides may be produced using any convenient protocol, where one is not limited to the use of labeled analogues that can be processed by a polymerase.

The above described three part hybridized complexes of the oligonucleotides tagged target nucleic acid, the probe nucleic acid and the oligonucleotide label are produced using any convenient protocol. Generally, the three components are brought together either sequentially or simultaneously under hybridization conditions sufficient to produce the hybridization complex through complementary base pairing between the various components. Generally, the hybridization conditions are high stringency conditions, e.g. where representative high stringency conditions are obtained by combining some subset of the following: high temperature (e.g. 60° C.), low monovalent cation concentration (e.g. 100 mM), chelation of divalent and trivalent cations (e.g. by 1 mM EDTA) and addition of co-solvents (e.g. 30% formamide). A typical high-stringency condition is 60° C., 750 mM monovalent cation, 6 mM EDTA, pH6.1.

In certain embodiments, the three part hybridized complex described above is produced by sequentially contacting the various components to each other under hybridization conditions. For example, the oligonucleotide tagged nucleic acid may be contacted first with the probe nucleic acid under hybridization conditions, e.g. by contacting the surface of array displaying the probe with the oligonucleotide tagged nucleic acid. Following this probe/target hybridization step, any resultant duplexes are then contacted with the labeled oligonucleotide under hybridization conditions, where the labeled oligonucleotide hybridizes to the corresponding oligonucleotide tags present on the duplexes to produce the three part hybridized complexes. The above order can also be reversed, such that the oligonucleotide tagged target nucleic acids and complementary labeled oligonucleotides are combined first under hybridization conditions to produce hybridization duplexes that are made up of the oligonucleotide tagged target nucleic acid and the labeled oligonucleotide. These duplexes are then contacted with the probe nucleic acids, e.g. by contacting the duplexes with an array of probe nucleic acids, to produce the three part hybridized complexes. In yet other embodiments, the labeled oligonucleotide may be contacted with the surface first, followed by contact of the surface with the oligonucleotide tagged target nucleic acid. In yet other embodiments, the various components are combined at substantially the same, if not the same time, such that the target and probe nucleic acids are contacted with each other in the presence of the labeled oligonucleotide under hybridization conditions to produce the three part hybridized complexes. In other words, all three components are contacted at least substantially simultaneously under hybridization conditions. In general, whether the components are contacted sequentially or simultaneously is not critical, so long as the three part complex is produced. To ensure that all of the target is labeled, a molar excess of labeled oligonucleotide is preferably employed, there the amount of excess is generally at least about 1.5-fold, usually at least about 1.75-fold and more usually at least about 2-fold.

In gene expression analyses in which the subject labeling methods are employed, the probe nucleic acids are typically present on the surface of a solid support, i.e. they are generally present in an array, as described previously. As such, the above steps result in the production of three part hybridization complexes across the surface of the array, where complexes on the array surface are formed between a probe nucleic acid at its complementary target nucleic acid. Following any desired washing step to remove unbound labeled oligonucleotide from the array surface, any three part hybridized complexes present on the array surface are detected.

The method employed to detect the complexes present on the surface may vary greatly depending on the label of the labeled oligonucleotide. For example, where the label is an isotopic label, a photographic image of the array may be obtained during the detection step. In those preferred embodiments in which the label is a fluorescent label, a device or devices capable of exciting the fluors and detecting the emitted signal are employed. A number of such devices suitable for use in detecting fluorescence on arrays are known to those of skill in the art and available from commercial sources. Representative fluorescence detection devices include the Affymetrix GeneArray Scanner (Affymetrix, Santa Clara, Calif.) and the Axon GenePix 4000™ microarray scanner (Axon Instruments, Foster City, Calif.).

The detected three part complexes on the array surface are then used to derive an expression profile of the cell from which the initial mRNA sample used to generate the target nucleic acids was derived. By expression profile is meant a collection of data that indicates which genes, or representative fraction thereof, of a genome of the cell are actually expressed. Since the only target nucleic acids that are contacted with the array surface are those that correspond to mRNAs originally present in the sample, three part complexes are produced at only those locations on the array surface where a probe resides that is complementary for the target nucleic acid and therefore corresponds to an mRNA from which the target nucleic acid was derived and a gene that was expressed in the cell from which the mRNA was derived. As such, by looking at the overall array of binding complexes on the array surface and knowing the identity of each probe on the array (i.e. the gene to which the probe corresponds), one can readily obtain an expression profile of the cell from which the target nucleic acids employed in the method were derived.

An important feature of the subject methods is that they are amenable to use in procedures where it is desired to hybridize two or more distinct target nucleic acid populations, e.g. target nucleic acid populations derived from different cells, to the same array, e.g. as in comparative gene expression analysis applications. In other words, the subject methods are suitable for use in so called "two color" applications, and are even suited for use in three or more different color analyses, in which a plurality of target nucleic acid populations each generated from a different initial mRNA sample are hybridized to the same array for detection, where each population must be indirectly labeled with a distinguishable label. In these embodiments, a separate oligonucleotide tagged target nucleic acid population is generated for each cell to be compared.

In certain of these embodiments, the oligonucleotide tag component of each type of tagged target nucleic acid differs. The different tags are chosen so that the expected tag-tag complement duplex melting temperatures are nearly identical, and so that the different tag sequences are sufficiently dissimilar to minimize the potential for inter-tag cross-talk (i.e. hybridization of a labeled tag complement to a tag different from its perfect complement). In other words, while the same oligonucleotide tag component is found in all of the tagged target nucleic acids generated from the same cell, the tag component differs between any two populations of target nucleic acids generated from different cell types. As a specific example, the tagged target nucleic acids for a first cell type will have a first oligonucleotide tag and the tagged target nucleic acids for a second cell type have a second oligonucleotide tag, where the first and second oligonucleotide tags differ from each other in terms of base sequence.

The differentially tagged populations of target nucleic acids are then combined with a corresponding number of different labeled oligonucleotides, one for each type of tagged nucleic acid, and the array, to produce the three part hybridized complexes, where contact of the components may be simultaneous or sequential, as described above. Preferably, the labels of the different labeled oligonucleotides are distinguishable from each other, such that they can be detected on the same array. For example, where the expression profile of two different cells is being compared, two different tagged target nucleic acid populations are produced, where each population differs from each by the nature of the oligonucleotide tag, as discussed above. These two populations may then be combined with two different types of labeled oligonucleotides which are labeled with distinguishable, e.g. fluorescent, labels, where the first type of labeled oligonucleotide hybridizes to the tag present in the first target nucleic acid population and the second type of labeled target oligonucleotide hybridizes to the second population of tagged target nucleic acids.

In yet other embodiments where multi-color analysis is desired, the oligonucleotide tags of each population may be the same. In these embodiments, following separate generation of each population of target nucleic acids, each population is separately contacted with a distinguishable label to produce populations of distinguishably labeled target nucleic acids. Each distinct type of distinguishable label employed in these embodiments shares a common region that is capable of hybridizing to the common oligonucleotide tag of all of the separate populations of target nucleic acids and a different label.

Following production of the three part complexes, as described above, and any washing step to remove unbound label, the three part complexes are then detected. The three part complexes produced from each different initial cell type can be distinguished from each other by the distinguishable labels associated with each cell type, even though the different populations of target nucleic acids have been hybridized to the same array. As such, one can readily compare the expression profiles of two or more different cells using the same array by practicing the subject methods, as described above.

In certain embodiments, the subject methods include a step of transmitting data from at least one of the detecting and deriving steps, as described above, to a remote location. By "remote location" is meant a location other than the location at the which the array is present and hybridization occur. For example, remote location could be another location (e.g. office, lab, etc.) in the same city, another location in a different city, another location in a different state, another location in a different country, etc. The data may be transmitted to the remote location for further evaluation and/or use. Any convenient telecommunications means may be employed for transmitting the data, e.g. facsimile, modem, internet, etc.

The subject methods finds use in a variety of applications. Especially facilitated by the subject methods are studies of differential gene expression in mammalian cells or cell populations. The cells may be from blood (e.g., white cells, such as T or B cells) or from tissue derived from solid organs, such as brain, spleen, bone, heart, vascular, lung, kidney, liver, pituitary, endocrine glands, lymph node, dispersed primary cells, tumor cells, or the like. Of interest is the use of the subject labeling methods in comparison expression analyses, as the subject methods can be easily employed to distinguishably label two or more different target nucleic acid populations for hybridization to the same array.

Kits

Also provided by the subject invention are kits for practicing the subject methods, as described above. The subject kits at least comprise a primer that includes the oligonucleotide tag domain, e.g. the promoter-tag-primers, discussed supra, and a corresponding labeled oligonucleotide, as described above. The subject kits may comprise one or more different tag primers and labeled oligonucleotides, e.g. one or more sets of complementary tag primers and labeled oligonucleotides, depending on whether it is desired to generate two or more differently tagged target nucleic acid populations, e.g. for use in gene expression comparison applications, as described above. The kits may further include a number of optional components, such as arrays of probe nucleic acids. Other reagents that may be present in the kits include: buffers, the appropriate nucleotide triphosphates (e.g. dATP, dCTP, dGTP, dTTP, ATP, CTP, GTP and UTP), reverse transcriptase, RNA polymerase, a reverse transcriptase inhibitor, where in many embodiments, the inhibitor is at least one ddNTP or a combination of ddNTPs, e.g. ddATP, ddGTP, ddCTP and/or ddTTP, etc. Also present in kits according to the subject invention is a set of instructions for practicing the subject methods, where the instructions may be associated with a package insert and/or the packaging of the kit or the components thereof. Finally, kits may contain software for use in the design of additional, mutually compatable tag sequences, as described above, where the software will include an algorithm for performing the desired steps recorded onto a computer readable storage medium.

The following examples are offered by way of illustration and not by way of limitation.

EXPERIMENTAL

I. Yeast Gene Expression Assay

A. Identification of Tag Sequence

Tag sequences to be introduced as a linker in the primer promoters described below were identified as follows. Tag sequences were designed based on the pattern of codon usage of the target organism, in this example Yeast, and the thermodynamic properties of the resultant sequences. In general, the rarest codons in any organism are the stop codons TAA(ochre), TAG (amber) and TGA (opal). Candidate sequences for yeast were built by forming random 27-mer concatamers of the following 7 building blocks:

| Nucleic Acid Sequence | Encoded Amino Acid Sequence | Yeast Frequency | Comment |
| --- | --- | --- | --- |
| CGTAGG | PR | 0.006% | stop (amber) in frame 3 |
| GTAGCG | VA | 0.005% | stop (amber) in frame 2 |
| TGA | stop | 0.055% | stop (opal) in frame 1 |
| TAA | stop | 0.102% | stop (ochre) in frame 1 |
| CGG | R | 0.124% | |
| CGC | R | 0.215% | |
| CGA | R | 0.224% | |
| TGC | C | 0.382% | |
| CTC | L | 0.429% | |

All frequencies are calculated in frame 1. Concatamers formed in this way contain at least one stop codon in every frame, are 63% GC, and should possess a tag sequence that is rare in the yeast genome.

The design criteria used to perform the initial design were: (1) the sequence should be observed to yield no close matches to yeast sequences (BLAST) search with seed size of 6); (2) the sequence should possess minimal self-structure; (3) the sequence should possess high melting temperature.

An initial list of 3127 unique 27mer concatamers yielded 16 candidates that met all of the criteria. The 16 candidates were then screened for subsets that possessed minimal potential for cross-hybridization. As a result, the following 2 T7(tag)T18VN primers were synthesized. In the following two primer-tag-promoters, the tag domain is in lower case:

```
T7 (tag1) T18VN
5'-AATTAATACGACTCACTATAGGGAGATtacgctactcatcgccggcgcctacg TTT   (SEQ ID NO:01)

TTTTTT TTTTTTTTVN-3'  (V = A/C/G, N = A/C/G/T)

T7 (tag2) T18VN
5'-AATTAATACGACTCACTATAGGGAGATcattacctacgtcggcgccgcgctac TTT   (SEQ ID NO:02)

TTTTTT TTTTTTTTVN-3'  (V = A/C/G, N = A/C/G/T)
```

The above primer-tag-promoters were employed to generate oligonucleotide tagged target nucleic acids from an initial yeast mRNA sample as described below.

B. Generation of Oligonucleotide Tagged Target Nucleic Acids from Two Different Yeast Cells Oligonucleotide tagged target nucleic acid was generated for two different yeast polyA$^+$RNA samples, using the following procedure for each sample. For sample 1, T7 (tag1) T18VN (SEQ ID NO:01) was employed as the primer-tag-promoter while for sample 2, T7 (tag2) T18VN (SEQ ID NO:02) was employed as the primer-tag-promoter. The following procedure was employed:

1. Add 400 ng polyA$^+$RNA from either yeast cell 1 or 2 to a reaction tube. Add 1.0 μl of the appropriate primer-tag-promoter (20 μM) and bring total sample volume to 11.5 μl in nuclease-free water. Incubate 70° C. for 10 min to denature primer and template. Quick chill on ice.
2. Mix the following components and maintain on ice. For more than one reaction, multiply by the number of reactions.

Master Mix A

| Component | Volume (μl) |
| --- | --- |
| 5 × First Strand Buffer* | 4.0 |
| 100 mM DTT | 2.0 |
| dNTPs (10 mM each) (Pharmacia) | 1.0 |
| Superscript II RT (200 U/μl) (Life Technologies, Inc.) | 1.0 |
| RNAGuard (36 U/μl) Pharmacia | 0.5 |
| Volume of cDNA Mix | 8.5 |

*250 mM Tris-HCl, pH 8.3, 15 mM MgCl$_2$, 375 mM KCl

3. Aliquot 8.5 μl of Master Mix A into each sample tube. Incubate first strand synthesis reaction at 40 ° C. for 60 min.

Composition of First Strand Synthesis Reaction

| Component | Final concentration or amount |
| --- | --- |
| polyA$^+$ RNA | 400 ng |
| Primer-Tag-Promoter | 1 μM |
| Tris-HCl, pH 8.3 | 50 mM |
| MgCl$_2$ | 3.0 mM |
| KCl | 75 mM |
| DTT | 10 mM |
| dNTPs | 0.5 mM each |
| Superscript II-RT | 200 U |
| RNAGuard | 18 U |
| Total reaction volume | 20 μl |

4. Mix the following components and maintain on ice. For more than one reaction, multiply by the number of reactions.

Master Mix B

| Component | Volume (μl) |
| --- | --- |
| 5 × First Strand Buffer | 4.0 |
| dNTPs (10 mM each) | 1.0 |
| MMLV-RT (50 U/μl) (Epicenter) | 1.0 |
| Nuclease-free water | 13 |
| Volume of master mix B | 20 |

5. Aliquot 20 μl of the Master Mix B into each sample tube. Incubate second strand synthesis reaction at 40° C. for 60 min.

Composition of Second Strand Synthesis Reaction

| Component | Final concentration or amount |
| --- | --- |
| Single Strand cDNA | Approximately 400 ng |
| Tris-HCl, pH 8.3 | 50 mM |
| MgCl$_2$ | 3 mM |
| KCl | 75 mM |
| DTT | 5 mM |
| dNTPs | 0.5 mM each |
| MMLV-RT | 50 U |
| Total reaction volume | 40 μl |

6. Immediately before use, mix the following components at room temperature. For more than one reaction, multiply by the number of reactions.

Master Mix C

| Component | Volume (μl) |
| --- | --- |
| Nuclease-free water | 0.8 |
| 5 × Transcription Buffer* | 16 |
| 100 mM DTT | 6.0 |
| NTPs (25 mM A, G, U, 7.5 mM CTP) (Pharmacia) | 8.0 |
| 400 mM MgCl$_2$ | 1.7 |
| ddATP (5.0 mM) (Pharmacia) | 0.8 |
| ddGTP (5.0 mM) (Pharmacia) | 0.8 |
| RNAGuard (36 U/μl) | 0.5 |
| Inorganic Pyrophosphatase (200 U/μl) | 0.6 |
| T7 RNA polymerase (2500 U/μl) Epicentre | 0.8 |
| Volume of Master Mix C | 36 |

*0.2 M Tris-HCl, pH 7.5, 50 mM NaCl, 30 mM MgCl$_2$, 10 mM spermidine (Epicentre)

7. Aliquot 40 μl of the master mix C into each sample tube. Incubate transcription reactions at 40° C. for 60 min.

Composition of Transcription Reaction

| Component | Final concentration or amount |
| --- | --- |
| Double-strand cDNA | Approximately 800 ng |
| Tris-HCl, pH 8.1 | 65 mM |
| MgCl$_2$ | 16 mM |
| KCl | 37.5 mM |
| NaCl | 10 mM |
| Spermidine | 2 mM |
| DTT | 10 mM |
| ATP, GTP, UTP | 2.5 mM each |
| CTP | 0.75 mM |
| ddATP, ddGTP | 50 μM each |
| T7 RNA polymerase | 2000 U |
| RNAGuard | 18 U |
| Inorganic pyrophosphatase | 0.12 U |
| Total reaction volume | 80 μl |

8. Add 20 μl 12×SSPE, 2% triton X-100 to each reaction tube to stop the reaction. Alternatively, if quantitation of the amplified RNA product is desired, purify the RNA from unincorporated nucleotides by precipitation of the cRNA products in 2.0 M LiCl. Measure the RNA concentration by absorbance at $OD_{260}$ using the conversion: 1 $OD_{260}$=40 μg/ml RNA.

The above procedure results in the generation of two distinct oligonucleotide tagged target nucleic acid populations, one derived from yeast sample 1 and one derived from yeast sample 2. The first target population is tagged with tag 1 and the second target population corresponding to yeast cell 2 is tagged with tag 2.

C. Labeled Oligonucleotides

The following labeled oligonucleotides were synthesized:

```
                                        (SEQ ID NO:03)
Cy3-ctag1:   5'-Cy3-CGTAGGCGCCGGCGATGAGTAGCGTAA-3'

(SEQ ID NO:04)
Cy5-ctag1:   5'-Cy5-CGTAGGCGCCGGCGATGAGTAGCGTAA-3'

(SEQ ID NO:05)
Cy3-ctag2:   5'-Cy3-GTAGCGCGGCGCCGACGTAGGTAATGA-3'

(SEQ ID NO:06)
Cy5-ctag2:   5'-Cy5-GTAGCGCGGCGCCGACGTAGGTAATGA-3'
```

D. Array Hybridization

An array displaying probes for a representative number of yeast genes is contacted with both populations of tagged target nucleic acids and a molar excess of Cy3-ctag1 and Cy5-ctag2, and the targets are allowed to hybridized to the probe nucleic acids in the presence of the labeled oligonucleotides. Genes expressed in yeast cell 1 are identified by detecting complexes labeled with Cy3 and genes expressed in yeast cell 2 are identified by detecting complexes labeled with Cy5.

E. Results

The above protocols provides a method for performing a two color gene expression analysis in which expressed genes from two different yeast cells are detected using the same array.

The above results and discussion demonstrate that subject methods provide a simple and efficient way of labeling nucleic acids, particularly target nucleic acids in gene expression analysis applications. Advantages of the subject methods include the ability to use a wide variety of fluorophores, not just those that can be processed by a polymerase. In addition, the subject methods can be readily employed in multi-color analyses, where two or more different target populations are hybridized to the same array. In addition, inexpensive reagents can be employed in the subject methods, making the subject methods economical. As such, the subject methods represent a significant contribution to the art.

All publications and patent application cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for comparing the expression profiles of at least two distinct samples, said method comprising:
   (a) enzymatically generating:
      (i) a first population of oligonucleotide tagged nucleic acids of differing sequence from an mRNA sample derived from a first sample, wherein each oligonucleotide tagged nucleic acid of said first population comprises a same first oligonucleotide tag; and
      (ii) a second population of oligonucleotide tagged nucleic acids of differing sequence from an mRNA sample derived from a second sample, wherein each oligonucleotide tagged nucleic acid of said second population comprises a same second oligonucleotide tag that differs from said first oligonucleotide tag;
   (b) hybridizing said first and second populations of oligonucleotide tagged target nucleic acids to an array of probe nucleic acids stably associated with the surface of a solid support, wherein said hybridizing occurs in the presence of:
      (i) first labeled oligonucleotide complementary to said first oligonucleotide tag of said first population; and
      (ii) second labeled oligonucleotide complementary to said second oligonucleotide tag of said second population; whereby hybridized complexes comprising said oligonucleotide tagged target nucleic acids, probe nucleic acids and labeled oligonucleotides are produced on the surface of said array;
   (c) detecting the presence of said hybridized complexes on said array surface;
   (d) deriving an expression profile for each of said samples from said detected hybridized complexes; and
   (e) comparing the derived expression profiles of each of said samples; whereby the expression profiles of said at least two distinct samples are compared.

2. The method according to claim 1, wherein said first and second labels are distinguishable.

3. The method according to claim 2, wherein said first and second labels are fluorescent.

4. The method according to claim 1, wherein a primer comprising an oligo dT domain and said oligonucleotide tag is employed in said enzymatically generating step.

5. The method according to claim 4, wherein said primer further comprises an RNA polymerase promoter.

6. A method for producing a population of detectably labeled nucleic acids, said method comprising:
   enzymatically generating from an mRNA source or sample by a linear amplification template dependent polymerization a population of oligonucleotide tagged nucleic acids of differing sequence using a primer comprising an oligonucleotide tag and template complementary region, wherein said oligonucleotide tagged nucleic acids in said population comprise the same oligonucleotide tag, and further wherein said oligonucleotide tagged nucleic acids in said population do not comprise a nucleotide residue modified to include a label moiety; and contacting said oligonucleotide tagged nucleic acids with labeled oligonucleotides complementary to said oligonucleotide tag under conditions sufficient for said labeled oligonucleotide to hybridize to said oligonucleotide tag, wherein the length of the labeled oligonucleotide is substantially the same as that of the oligonucleotide tag;

whereby a population of detectably labeled nucleic acids is produced.

7. The method according to claim 6, wherein said detectably labeled nucleic acids are directly detectable.

8. The method according to claim 7, wherein said directly detectable label is fluorescent.

9. A method for producing a detectably labeled population of target nucleic acids from an initial nucleic acid sample, said method comprising:

enzymatically generating from an mRNA source or sample a population of oligonucleotide tagged target nucleic acids of differing sequence from an initial nucleic acid sample using a primer comprising an oligonucleotide tag and template complementary region, wherein said oligonucleotide tagged target nucleic acids in said population comprise the same oligonucleotide tag, and further wherein said oligonucleotide tagged nucleic acids in said population do not comprise a nucleotide residue modified to include a label moiety; and contacting said population of oligonucleotide tagged target nucleic acids with labeled oligonucleotides complementary to said oligonucleotide tag of each oligonucleotide tagged target nucleic acid under hybridization conditions, wherein the length of the labeled oligonucleotide is substantially the same as that of the oligonucleotide tag;

whereby a detectably labeled population of target nucleic acids is produced.

10. The method according to claim 9, wherein said primer comprises an oligo dT domain.

11. The method according to claim 10, wherein said primer further comprises an RNA polymerase promoter domain.

12. The method according to claim 10, wherein said population of detectably labeled target nucleic acids is labeled with a fluorescent label.

13. A method of detecting the presence of a nucleic acid analyte in a target sample, said method comprising:

(a) enzymatically generating from an mRNA source or sample by linear amplification a population of oligonucleotide tagged target nucleic acids of differing sequence from said nucleic acid analyte, wherein said oligonucleotide tagged target nucleic acids in said population comprise the same oligonucleotide tag, and further wherein said oligonucleotide tagged target nucleic acids in said population do not comprise a nucleotide residue modified to include a label moiety; and (b) producing a three-part hybridized complex that comprises:

(i) an oligonucleotide tagged target nucleic acid from said population of oligonucleotide tagged target nucleic acids;

(ii) a labeled oligonucleotide hybridized to said oligonucleotide tag, wherein the length of the labeled oligonucleotide is substantially the same as that of the oligonucleotide tag; and (iii) a probe nucleic acid, wherein said probe nucleic acid does not hybridize to the oligonucleotide tag of said oligonucleotide tagged target nucleic acid;

(c) detecting the presence of said hybridized complex; and (d) relating the presence of said hybridized complex to the presence of said nucleic acid analyte in said sample; whereby the presence of said nucleic acid analyte in said sample is detected.

14. The method according to claim 13, wherein said probe is stably associated with the surface of a solid support.

15. The method according to claim 13, wherein said probe is present on an array.

16. The method according to claim 13, wherein said labeled oligonucleotide is fluorescently labeled.

17. The method according to claim 13, wherein a primer comprising an oligo dT region and said oligonucleotide tag is employed in said enzymatically generating step.

18. The method according to claim 17, wherein said primer further comprises an RNA polymerase promoter.

19. The method according to claim 13, wherein said method further comprises transmitting data obtained from at least one of said detecting and related steps to a remote location.

20. A method for obtaining an expression profile for a cell, said method comprising:

(a) enzymatically generating a population of oligonucleotide tagged nucleic acids of differing sequence from an mRNA sample derived from said cell, using a primer comprising an oligonucleotide tag and template complementary region, wherein each oligonucleotide tagged nucleic acid comprises a same oligonucleotide tag, and further wherein said oligonucleotide tagged nucleic acids in said population do not comprise a nucleotide residue modified to include a label moiety;

(b) producing at least one three-part hybridized complex comprising:

(i) an oligonucleotide tagged nucleic acid from said population of oligonucleotide tagged nucleic acids;

(ii) a labeled oligonucleotide hybridized to said oligonucleotide tag, wherein the length of the labeled oligonucleotide is substantially the same as that of the oligonucleotide tag; and (iii) a probe nucleic acid stably associated with the surface of a solid support, wherein said probe nucleic acid does not hybridize to the oligonucleotide tag of said oligonucleotide tagged nucleic acid;

(c) detecting the presence of said at least one hybridized complex on said surface of said solid support; and (d) deriving an expression profile for said cell from said detected at least one hybridized complex; whereby said expression profile for said cell is obtained.

21. The method according to claim 20, wherein a primer comprising an oligo dT domain and said oligonucleotide tag is employed in said enzymatically generating step.

22. The method according to claim 21, wherein said primer further comprises an RNA polymerase promoter.

23. The method according to claim 20, wherein said labeled oligonucleotide is fluorescently labeled.

24. The method according to claim 20, wherein said method further comprises transmitting data obtained from at least one of said detecting and deriving steps to a remote location.

* * * * *